US010617641B2

(12) United States Patent
Jeong

(10) Patent No.: US 10,617,641 B2
(45) Date of Patent: Apr. 14, 2020

(54) COMPOSITION FOR PREVENTING OR TREATING ISCHEMIC DISEASES, CONTAINING LIPOSOMES IN WHICH VEGF-DERIVED PEPTIDES ARE SUPPORTED

(71) Applicant: INDUSTRIAL COOPERATION FOUNDATION CHONBUK NATIONAL UNIVERSITY, Jeollabuk-do (KR)

(72) Inventor: Hwan Jeong Jeong, Jeollabuk-do (KR)

(73) Assignee: INDUSTRIAL COOPERATION FOUNDATION CHONBUK NATIONAL UNIVERSITY, Jeollabuk-do (KR)

( * ) Notice: Subject to any disclaimer, the term of this patent is extended or adjusted under 35 U.S.C. 154(b) by 0 days.

(21) Appl. No.: 15/571,786

(22) PCT Filed: May 23, 2016

(86) PCT No.: PCT/KR2016/005453
§ 371 (c)(1),
(2) Date: Nov. 3, 2017

(87) PCT Pub. No.: WO2016/190642
PCT Pub. Date: Dec. 1, 2016

(65) Prior Publication Data
US 2018/0263908 A1 Sep. 20, 2018

(30) Foreign Application Priority Data
May 27, 2015 (KR) ........................ 10-2015-0074257

(51) Int. Cl.
| A61K 38/00 | (2006.01) |
| A61K 9/127 | (2006.01) |
| A61K 51/04 | (2006.01) |
| A61K 51/12 | (2006.01) |
| A61P 9/10 | (2006.01) |
| A61K 9/00 | (2006.01) |
| A61K 38/18 | (2006.01) |

(52) U.S. Cl.
CPC .......... *A61K 9/1271* (2013.01); *A61K 9/0019* (2013.01); *A61K 38/1866* (2013.01); *A61K 51/048* (2013.01); *A61K 51/0478* (2013.01); *A61K 51/1234* (2013.01); *A61P 9/10* (2018.01)

(58) Field of Classification Search
None
See application file for complete search history.

(56) References Cited

U.S. PATENT DOCUMENTS

2012/0141424 A1 6/2012 Alitalo et al.
2013/0195764 A1 8/2013 Kim et al.

OTHER PUBLICATIONS

Hwang et al. Radiology: vol. 273: No. 1, p. 160-167, Oct. 2014.*
Scott et al. The FASEB Journal vol. 23, 02261-3366, Oct. 2009.*
Stuttfeld and Ballmer-Hofer, IUBMB Life, 61(9): 915-922, Sep. 2009.*
VEGFA—Vascular endothelial growth factor A precursor—*Homo sapiens* (Human) UniProtKB—P15692 (VEGFA_HUMAN), last visited 2019.*
Bunevicius et al., "The Potential Roles of $^{18}$F-FDG-PET in Management of Acute Stroke Patients," *BioMed Research International*, 2013, pp. 1-14.
Hwang et al., "Peptide-loaded Nanoparticles and Radionuclide Imaging for Individualized Treatment of Myocardial Ischemia," *Radiology*, 273(1): 2014, pp. 160-167.
Khan et al., "Gene therapy progress and prospects: therapeutic angiogenesis for limb and myocardial ischemia," *Gene Therapy*, 10(4): 2003, pp. 285-291.
Levchenko et al., "Liposomes in Diagnosis and Treatment of Cardiovascular Disorders," *Methodist DeBakey Cardiovascular Journal*, 8(1): 2012, pp. 36-41.
Mäkinen et al., "Increased Vascularity Detected by Digital Subtraction Angiography after VEGF Gene Transfer to Human Lower Limb artery: A Randomized, Placebo-Controlled, Double-Blinded Phase II Study," *Molecular Therapy*, 6(1): 2002, pp. 127-133.
Nagasawa et al., "Correlation Between Cerebral Blood Flow and Histologic Changes in a New Rat Model of Middle Cerebral Artery Occlusion," *Stroke*, 20(8): 1989, pp. 1037-1043.

(Continued)

*Primary Examiner* — Jeanette M Lieb
(74) *Attorney, Agent, or Firm* — Norton Rose Fulbright US LLP

(57) ABSTRACT

The present invention relates to: a pharmaceutical composition for preventing or treating ischemic diseases, containing liposomes into which vascular endothelial growth factor (VEGF)-derived peptides are loaded; a method for treating ischemic diseases, comprising the step of administering the pharmaceutical composition to an individual suspected of having an ischemic disease; a use of the liposomes; and a kit for evaluating, using the liposomes, the amount of liposomes, into which VEGF-derived peptides are loaded, delivered to ischemic lesions and of loaded materials released and absorbed. The composition, of the present invention, for preventing or treating ischemic diseases, containing liposomes into which VEGF-derived peptides are loaded, the liposomes having an average particle size of 90 to 110 nm and a particle distribution of 50 to 200 nm and being surface-modified with polyethylene glycol, is capable of significantly increasing the absorption of VEGF compared with treatment using solely VEGF, thereby effectively treating ischemic diseases such as myocardial infarction, middle cerebral artery stenosis, lower limb ischemia, and cerebral infarction. In addition, the kit provided in the present invention can be useful in evaluating the amount of liposomes, into which VEGF-derived peptides are loaded, delivered to ischemic lesions and of loaded materials released and absorbed, in a treatment step for a patient with ischemic diseases.

6 Claims, 8 Drawing Sheets

Specification includes a Sequence Listing.

(56) References Cited

OTHER PUBLICATIONS

Scott et al., "Targeting VEGF-encapsulated immunoliposomes to MI heart improves vascularity and cardiac function," *The FASEB Journal*, 23(10): 2009, pp. 3361-3367.
Ylä-Herttuala et al., "Gene transfer as a tool to induce therapeutic vascular growth," *Nature Medicine*, 9(6): 2003, pp. 694-701.

* cited by examiner

PBS

VEGF

PEG-LP(VEGF) / 5.4E-9 M

PEG-LP(VEGF) / 5.0E-10 M

PEG-LP(VEGF) / 2.5E-10 M

SEQUENCE LISTING

<160> NUMBER OF SEQ ID NOS: 1

<210> SEQ ID NO 1
<211> LENGTH: 11
<212> TYPE: PRT
<213> ORGANISM: Artificial
<220> FEATURE:
<223> OTHER INFORMATION: VEGF peptide

<400> SEQUENCE: 1

Met Arg Ile Lys Pro His Gln Gly Gln His Ile
1               5                   10

COMPOSITION FOR PREVENTING OR TREATING ISCHEMIC DISEASES, CONTAINING LIPOSOMES IN WHICH VEGF-DERIVED PEPTIDES ARE SUPPORTED

CROSS-REFERENCE TO RELATED APPLICATIONS

This application is a national phase application under 35 U.S.C. § 371 of International Application No. PCT/KR2016/005453, filed May 23, 2016, which claims priority to Korean Patent Application No. 10-2015-0074257, filed May 27, 2015, the disclosure of which applications are incorporated herein by reference in their entirety.

FIELD OF THE DISCLOSURE

The present invention relates to a composition for preventing or treating an ischemic disease, including liposomes into which a vascular endothelial growth factor (VEGF)-derived peptide is loaded, a method for treating an ischemic disease, which includes administering the pharmaceutical composition to a subject suspected of having the ischemic disease, a use of the liposomes, and a kit for assessing a degree of delivery of the liposomes, into which the VEGF-derived peptide is loaded, to ischemic lesions and degrees of release and uptake of a loaded material. More particularly, the liposomes into which the VEGF-derived peptide is loaded and which have a particle distribution of 50 to 200 nm with an average particle size of 100 nm and have a surface modified with polyethylene glycol can be effectively used for the composition for preventing and treating an ischemic disease because the liposomes can increase the uptake of the VEGF-derived peptide. Also, the kit provided in the present invention can be useful in assessing a degree of delivery of the liposomes, into which the VEGF-derived peptide is loaded, to ischemic lesions and degrees of release and uptake of the loaded material because two types of the liposomes, which are prepared in a state in which a chelate is bound and not bound to PE as a structural component of the liposomes are labeled with radioactive nuclides and a radioactive compound including the radioactive nuclides, respectively.

DESCRIPTION OF RELATED ART

Ischemic diseases include cardiovascular diseases caused by the restriction of blood supply, and myocardial ischemia and ischemic peripheral vascular diseases belong to these diseases. Among such ischemic diseases, the cardiovascular diseases have ranked as the leading cause of death in Korea. In addition to the ischemic diseases, cerebrovascular diseases and lower limb ischemia belong to the three major ischemic diseases. Owing to the western dietary lifestyles and the advent of an aging era in Korea, the incidence of such ischemic diseases has increased, and thus research on treatment of these diseases has been actively conducted.

With the recent finding of the mechanism of angiogenesis, attempts have been made to treat ischemic diseases by administering a gene or protein of an angiogenesis-related factor to an ischemic area to induce neovascularization, which leads to an increased collateral flow. Among these, a vascular endothelial growth factor (VEGF) is a protein that specifically grows and differentiates vascular endothelial cells and is known to be generally associated with the neovascularization, and genes inducing the neovascularization, such as VEGF genes, have been used to treat the ischemic diseases in order to restore blood flow in occluded blood vessels (Yla-Herttuala S and Alitalo K, Nat Med., 9(6):694-701, 2003; Khan T A et al., Gene Ther., 10(4):285-91, 2003).

However, a method of administering an angiogenic recombinant protein such as VEGF has the following problems. 1) Because the injected angiogenic protein migrates into other tissues or loses its activity, a large amount of a high-purity protein should be used to have an angiogenic effect, which entails great expense. 2) It is desirable to continuously administer a small volume of the protein in order to form collateral vessels, but the protein has a problem in that it should be frequently injected. The aforementioned problems may be solved using a delivery system capable of slowly releasing the angiogenic protein while staying in an injected area. Also, a tracking strategy capable of effectively predicting a therapeutic effect by exactly monitoring an in vivo distribution of such an injection delivery system is required.

For this purpose, various types of research have been conducted, and an adenoviral gene delivery system (Ad.VEGF) into which VEGF was introduced was tested using an ischemic myocardial and muscle cell model. As a result, although it was confirmed that the blood vessel counts increased (Mkinen K et al., Mol. Ther., 6, 127-133, 2002), a viral vector system has a problem concerning stability. Therefore, there is a need for development of a delivery system which is safe for human bodies and can increase a VEGF uptake rate.

Accordingly, the present inventors have conducted ardent research to increase the VEGF uptake rate to enhance a therapeutic effect on ischemic diseases, and found that liposomes which have a particle size distribution of 50 to 200 nm with an average particle size of 100 nm and have a surface modified with polyethylene glycol and into which a VEGF-derived peptide is loaded at a concentration of $2.5 \times 10^{-10}$ M or more increase a VEGF uptake rate in an ischemic lesion to enhance a therapeutic effect on the ischemic diseases when the liposomes are used as a drug delivery system. Therefore, the present invention has been completed based on the facts.

SUMMARY OF THE INVENTION

It is an aspect of the present invention to provide liposomes into which a VEGF-derived peptide is loaded, which is able to enhance a therapeutic effect on ischemic diseases.

To solve the above problems, according to one aspect of the present invention, there is provided a pharmaceutical composition for preventing or treating an ischemic disease, which includes liposomes into which a VEGF-derived peptide is loaded. Here, the liposomes have a surface modified with polyethylene glycol, and have a particle distribution of 50 to 200 nm with an average particle size of 90 to 110 nm.

According to one preferred embodiment of the present invention, the VEGF-derived peptide may consist of an amino acid sequence set forth in SEQ ID NO: 1.

According to another preferred embodiment of the present invention, the liposomes into which the VEGF-derived peptide is loaded at a concentration of $2.5 \times 10^{-10}$ M or more may be included.

According to still another preferred embodiment of the present invention, the liposomes may be prepared using a method which includes (a) dissolving L-α-phosphatidylcholine (Egg PC), cholesterol (CH), and 1,2-distearoyl-sn-glycero-3-phosphoethanolamine-N-[methoxy(polyethyleneglycol)-2000] (PEG2000-DSPE) to which polyethylene glycol (PEG2000) is bound in an organic solvent and evaporating the organic solvent to obtain a lipid thin film having a surface modified with polyethylene glycol; (b) completely hydrating the obtained thin film in a solution including a VEGF-derived peptide to prepare liposomes into which the VEGF-derived peptide is loaded; and (c) extruding the liposomes through a porous membrane to obtain the liposomes into which the VEGF-derived peptide is loaded, wherein the liposomes have an average particle size of 90 to 110 nm and a particle distribution of 50 to 200 nm.

According to yet another preferred embodiment of the present invention, the L-α-phosphatidylcholine, the cholesterol, and the PEG2000-DSPE may be dissolved at a ratio of 50:40:10 in step (a).

According to yet another preferred embodiment of the present invention, the organic solvent in step (a) may be a mixed solvent of chloroform and methanol.

According to yet another preferred embodiment of the present invention, the evaporation in step (a) may be performed at 45 to 55° C. for 3 hours to 5 hours.

According to yet another preferred embodiment of the present invention, the hydration process in step (b) may be performed at 35 to 39° C. for 1 hour to 2 hours in a PBS buffer solution including the VEGF-derived peptide.

According to yet another preferred embodiment of the present invention, the polyethylene glycol may have a molecular weight of 1,800 g/mol to 2,200 g/mol.

According to yet another preferred embodiment of the present invention, the ischemic disease may include one or more selected from the group consisting of myocardial infarction, middle cerebral artery occlusion, lower limb ischemia, and cerebral infarction.

According to yet another preferred embodiment of the present invention, the composition may be an injectable formulation.

According to another aspect of the present invention, there is provided a kit for assessing a degree of delivery of liposomes, into which a VEGF-derived peptide is loaded, to ischemic lesions and degrees of release and uptake of a loaded material, which includes (a) liposomes into which a VEGF-derived peptide is loaded; and (b) liposomes into which the VEGF-derived peptide is loaded and to which a chelate having a functional group capable of labeling PE of the liposomes with radioactive nuclides is bound, wherein the liposomes of (a) are labeled with a radioactive compound including radioactive nuclides, and the liposomes of (b) are labeled with the radioactive nuclides.

According to the present invention, the composition for preventing or treating an ischemic disease, which includes liposomes into which a VEGF-derived peptide is loaded and which have a particle distribution of 50 to 200 nm with an average particle size of 90 to 110 nm and have a surface modified with polyethylene glycol, can remarkably increase the uptake of VEGF, compared to when treated with VEGF alone, and thus can be used to effectively treat ischemic diseases such as myocardial infarction, middle cerebral artery occlusion, lower limb ischemia, and cerebral infarction.

Also, a liposome kit including DTPA-PE provided in the present invention can be useful in assessing a degree of delivery of the liposomes, into which the VEGF-derived peptide is loaded, to ischemic lesions and degrees of release and uptake of a loaded material during a process of curing a patient suffering from ischemic diseases.

DETAILED DESCRIPTION OF THE INVENTION

Figure 1:
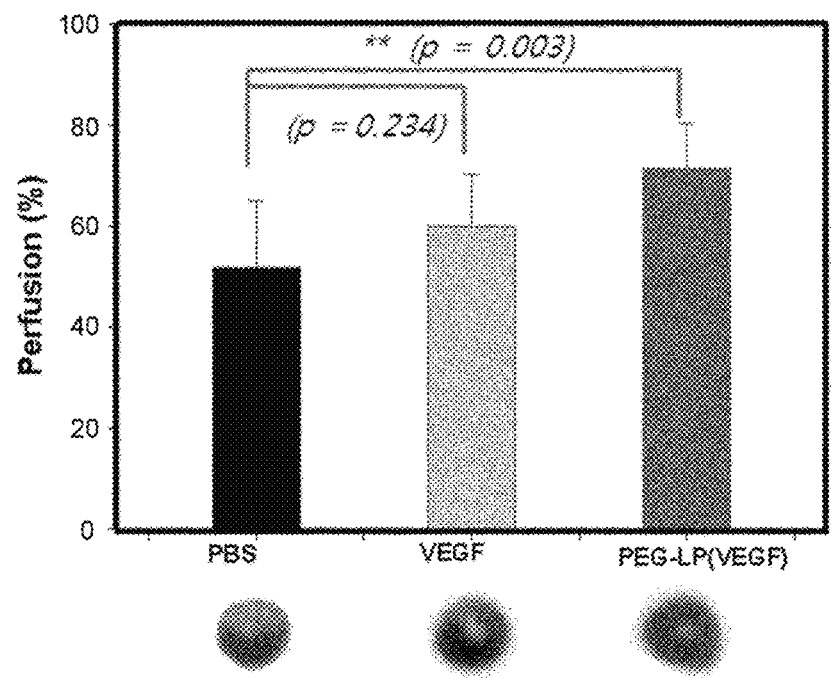
FIG. 1 shows data of measuring changes in cardiac perfusion after one week has elapsed since each of the control (PBS), a VEGF-derived peptide (VEGF), and liposomes of the present invention into which the VEGF-derived peptide is loaded {PEG-LP(VEGF)} is injected into myocardial infarction-induced rats through an apical puncture.

Hereinafter, the present invention will be described in further detail.

As described above, although treatment using VEGF to treat ischemic diseases has come into the spotlight, a method of administering an angiogenic recombinant protein such as VEGF has problems in that a large amount of the high-purity protein should be administered or a small volume of the protein should be continuously administered. Therefore, it is necessary to construct a delivery system capable of slowly releasing the angiogenic protein while staying in an injected area or increasing an uptake rate in lesion tissues.

The present invention sought to solve the above problems by providing a composition for preventing or treating an ischemic disease, which includes liposomes into which a VEGF-derived peptide is loaded. For this purpose, the liposomes which have a surface modified with polyethylene glycol and have a particle distribution of 50 to 200 nm and an average particle size of 90 to 110 nm are provided. In this case, the liposomes may be effectively used for the composition for preventing and treating an ischemic disease because the liposomes may increase the uptake of the VEGF-derived peptide.

Therefore, the present invention provides a pharmaceutical composition for preventing or treating an ischemic disease, characterized by including liposomes into which the VEGF-derived peptide is loaded. Here, the liposomes have a surface modified with polyethylene glycol, and have an average particle size of 90 to 110 nm and a particle distribution of 50 to 200 nm.

Commercially available VEGF-derived peptides may be generally used without limitation as the VEGF-derived peptide. Preferably, a peptide consisting of an amino acid sequence of Ac-MRIKPHQGQHI-NH2 (SEQ ID NO: 1) may be used.

The liposomes may be prepared using a method which includes:

(a) dissolving L-α-phosphatidylcholine (Egg PC), cholesterol (CH), and 1,2-distearoyl-sn-glycero-3-phosphoethanolamine-N-[methoxy(polyethyleneglycol)-2000] (PEG2000-DSPE) in an organic solvent and evaporating the organic solvent to obtain a lipid thin film having a surface modified with polyethylene glycol;

(b) completely hydrating the obtained thin film in a solution including the VEGF-derived peptide to prepare liposomes into which the VEGF-derived peptide is loaded; and (c) extruding the liposomes through a porous membrane to obtain the liposomes into which the VEGF-derived peptide is loaded, wherein the liposomes have an average particle size of 90 to 110 nm and a particle distribution of 50 to 200 nm.

The method will be described in further detail, as follows. In step (a), the L-α-phosphatidylcholine, the cholesterol and the PEG2000-DSPE are characterized by being mixed at a ratio of 50:40:10. In this case, solvents generally used herein may be used without limitation as the organic solvent in step (a), and solvents such as an alcohol such as methanol or butanol, ethyl acetate, chloroform, or hexane may be used alone or in combination. Preferably, a mixed solvent of chloroform and methanol, and more preferably a mixed solvent of chloroform and methanol at a ratio of 7:3 may be used. Also, the evaporation in step (a) may be performed at 45 to 55° C. for 3 hours to 5 hours.

The polyethylene glycol in step (a) may have a molecular weight of 1,800 g/mol to 2,200 g/mol. Preferably, polyethylene glycol having a molecular weight of 2,000 g/mol may be used, and commercially available polyethylene glycol may be used without limitation.

The hydration process in step (b) may be performed at 35 to 39° C. for 1 hour to 2 hours. Here, the liposomes may be preferably prepared by hydrating a lipid thin film in a PBS buffer solution including the VEGF-derived peptide.

Also, the extrusion in step (c) may be performed using polycarbonate membranes having pore sizes of 400 nm, 200 nm, 100 nm, and 50 nm. After the extrusion process, size exclusion chromatography may be further performed to remove VEGF which is not loaded into the liposomes.

According to one aspect of the present invention, experiments for comparison with a group in which rats are treated with the VEGF-derived peptide alone are performed to determine whether the liposomes into which the VEGF-derived peptide is loaded as prepared by the method increase therapeutic efficacy against ischemic diseases. The results are shown in FIGS. 1 and 2.

Figure 2:
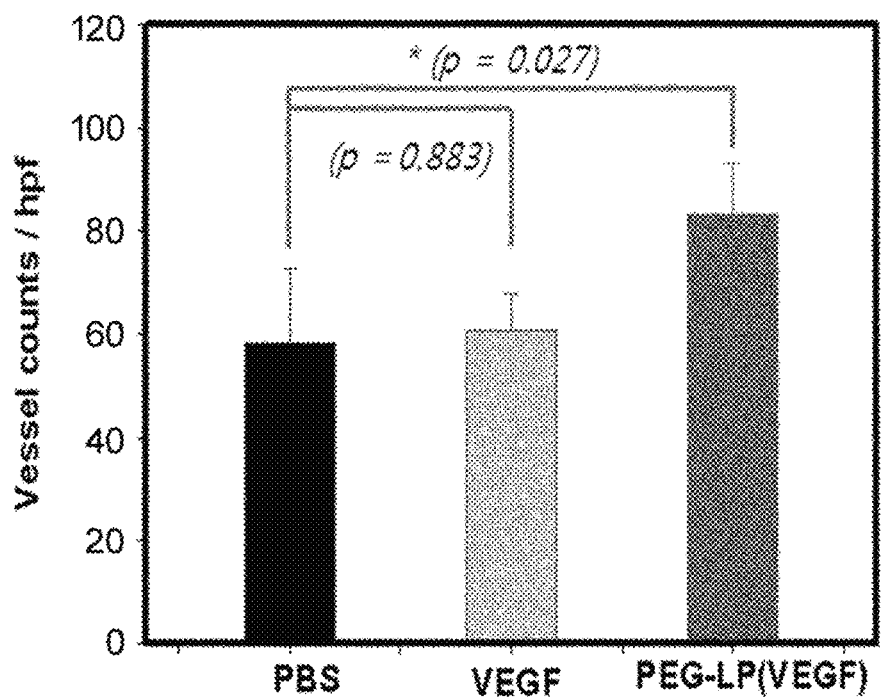
FIG. 2 shows data showing the total blood vessel counts obtained by extracting ischemic tissues and measuring the ischemic tissues through immunostaining after one week has elapsed since each of the control (PBS), a VEGF-derived peptide (VEGF), and liposomes of the present invention into which the VEGF-derived peptide is loaded {PEG-LP(VEGF)} is injected into myocardial infarction-induced rats through an apical puncture.

As shown in FIGS. 1 and 2, it is confirmed that a perfusion-improving effect and a significant increase in total vessel counts are not observed in the group in which the liposomes are treated with the VEGF-derived peptide alone, compared to the control in which a PBS solution is injected, whereas the perfusion is statistically significantly improved and the total vessel counts are increased in a group in which rats are treated with the liposomes into which the VEGF-derived peptide is loaded (LP-VEGF), compared to the control.

Figure 3:
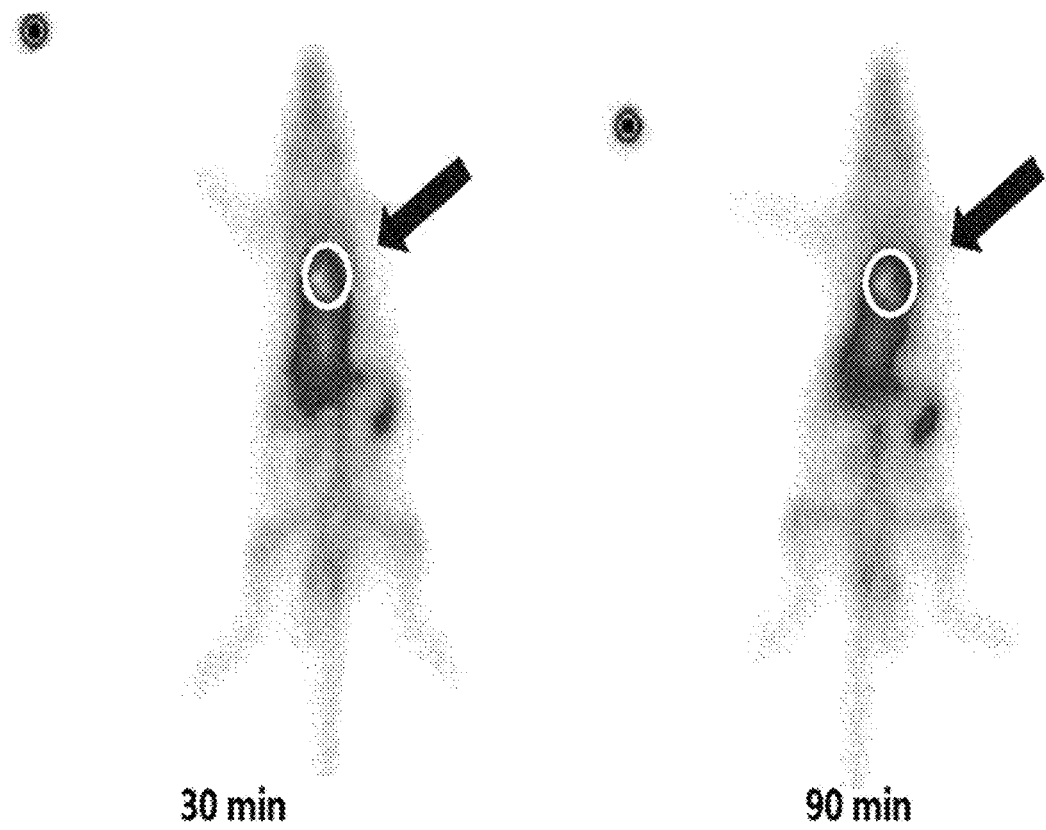
FIG. 3 shows data showing a gamma image observed after 30 minutes and 90 minutes has elapsed since liposomes labeled with $^{99}$mTc-HMPAO are injected into rats having a myocardial infarction model through an apical puncture in order to compare VEGF uptake rates of the liposomes of the present invention into which the VEGF-derived peptide is loaded {PEG-LP(VEGF)}.

FIG. 3 shows results of determining a change in uptake rate in ischemic lesions according to time elapsed from a gamma image obtained by labeling the liposomes into which the VEGF-derived peptide is loaded with $^{99m}$Tc-HMPAO and injecting the liposomes into rats. Here, it is confirmed that it is suitable to compare the result values 90 minutes after injection of the liposomes in order to eliminate an effect of a blood pool of the heart and compare the results of uptake in the ischemic lesions.

Figure 4:
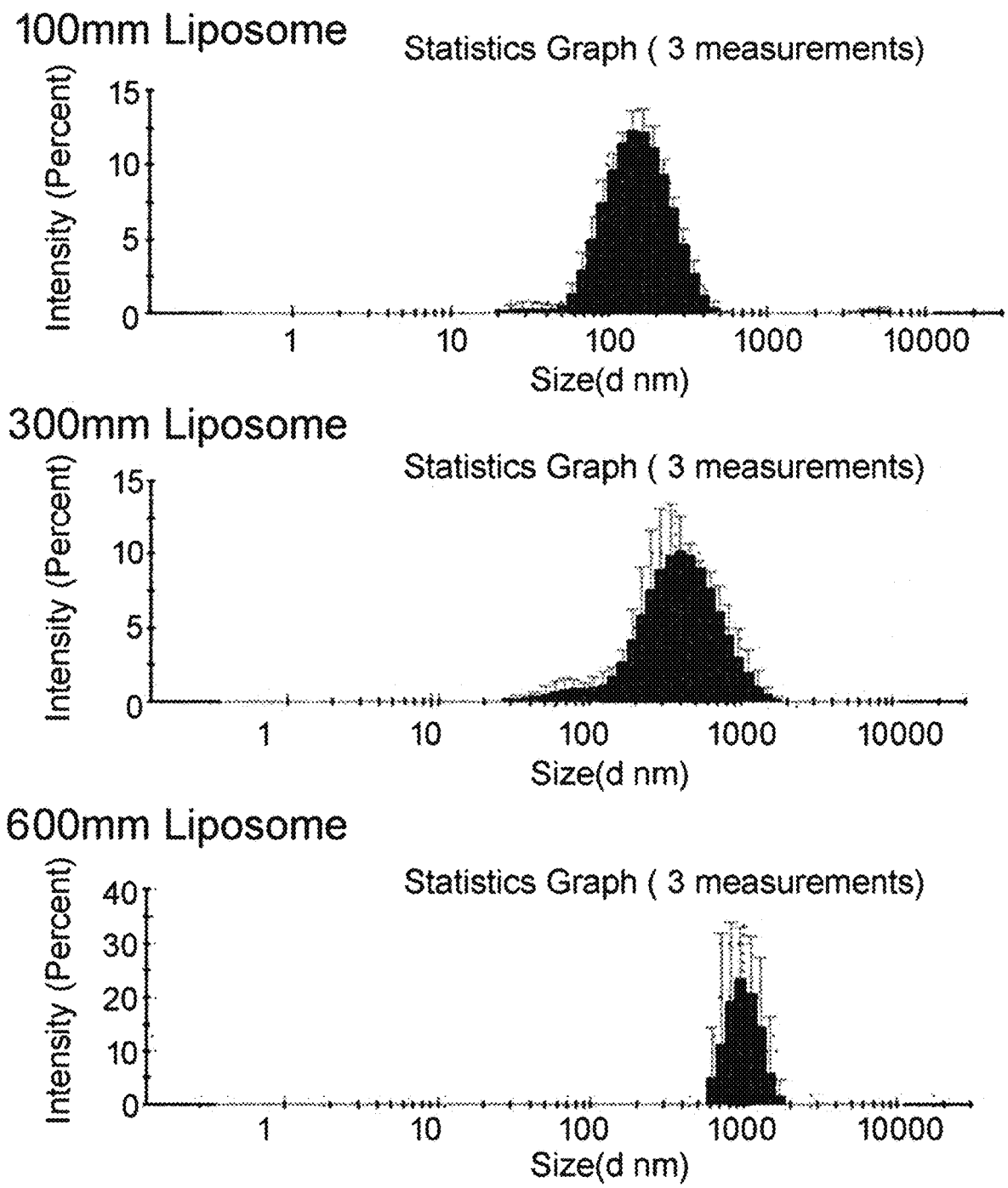
FIG. 4 shows data of particle distribution obtained by preparing liposomes of the present invention into which the VEGF-derived peptide is loaded {PEG-LP(VEGF)} so that the liposomes have average particle sizes of 100 nm, 300 nm and 600 nm and measuring the liposomes using a dynamic light scattering system (DLS; Malvern Instruments Limited, Melvern, the United Kingdom) as a particle size analyzer.

FIG. 4 shows particle distributions of the liposomes into which the VEGF-derived peptide is loaded {PEG-LP (VEGF)}, the liposomes having average particle sizes of 100 nm, 300 nm and 600 nm, respectively. Here, it is confirmed that the liposomes have a particle distribution of 50 to 200 nm when the liposomes have an average particle size of 100 nm.

Figure 5:
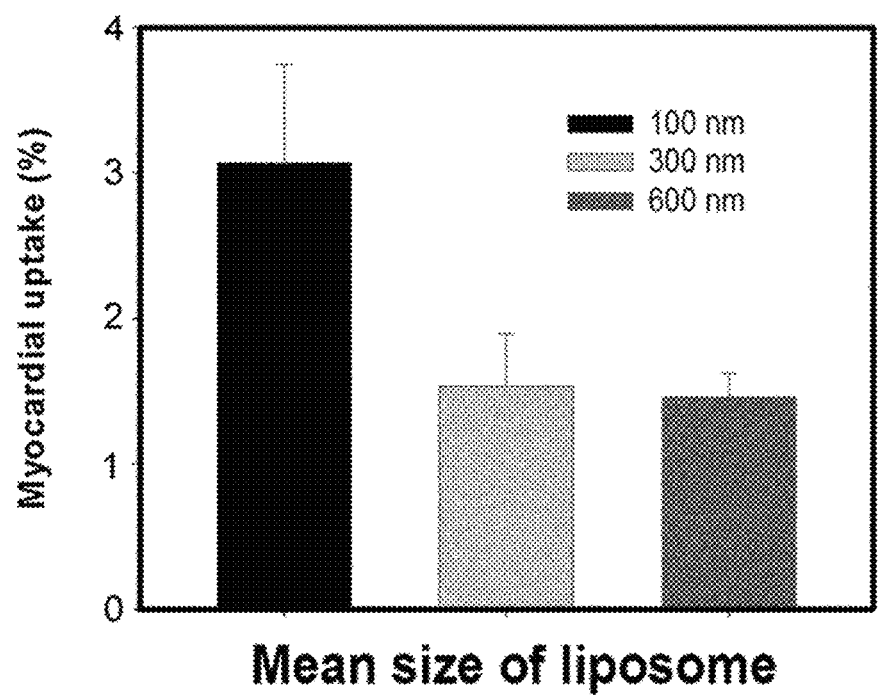
FIG. 5 shows data of observing the uptake rates in the heart having ischemic lesions from a gamma image obtained after 90 minutes has elapsed since the liposomes of the present invention into which the VEGF-derived peptide is loaded {PEG-LP(VEGF)} and which have different sizes and are labeled with $^{99}$mTc-HMPAO are injected into rats having a myocardial infarction model.

Also, FIG. 5 is a diagram showing an effect of the size of the liposomes into which the VEGF-derived peptide is loaded on the uptake of the liposomes in ischemic lesions.

Here, it is confirmed that, when the liposomes have a large average particle size, the uptake rate in the ischemic lesions drastically decreases, and confirmed that, when the liposomes have an average particle size of approximately 100 nm, the highest uptake rate is observed. When the average particle size of the liposomes is less than 50 nm, a rate of loaded VEGF is very low, and the loaded VEGF may not be easily released due to a broken structure of the liposomes, resulting in a reduced therapeutic effect.

Figure 6:
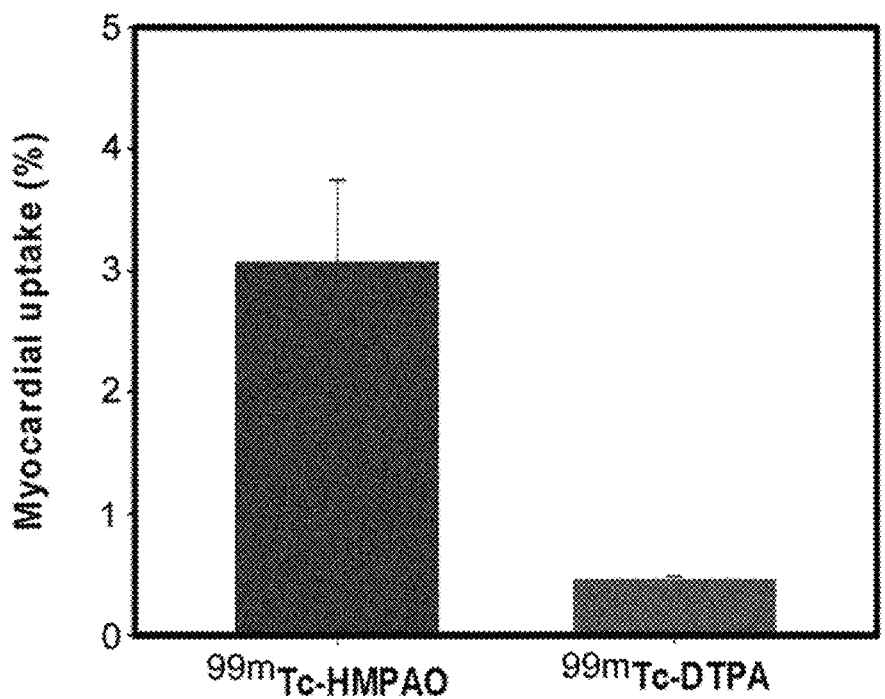
FIG. 6 shows data of comparing the uptake rates in the heart having ischemic lesions from a gamma image obtained after 90 minutes has elapsed since the liposomes of the present invention into which the VEGF-derived peptide is loaded {PEG-LP(VEGF)} are labeled with $^{99}$mTc-HMPAO and $^{99}$mTc-DTPA, respectively, and injected into rats having a myocardial infarction model.

According to another aspect of the present invention, to determine to which extent the liposomes or the VEGF loaded into the liposomes are actually absorbed in the ischemic lesions, a modified radiolabeling method is performed to compare the uptake rates of the liposomes. As a result, it can be seen that a difference between a value of the liposomes labeled with $^{99m}$Tc-HMPAO and a value of the liposomes labeled with $^{99m}$Tc using DTPA is a value of $^{99m}$Tc-HMPAO released from the liposomes, and the release and uptake in the ischemic lesions occur at high levels, as shown in FIG. 6, indicating that the uptake of the liposomes occurs in the ischemic lesions. In effect, this suggests that the VEGF loaded into the liposomes is released at a high rate in the ischemic lesions, and the liposomes are absorbed in the ischemic lesions, thereby causing an increase in therapeutic effect in the ischemic lesions.

Figure 7:
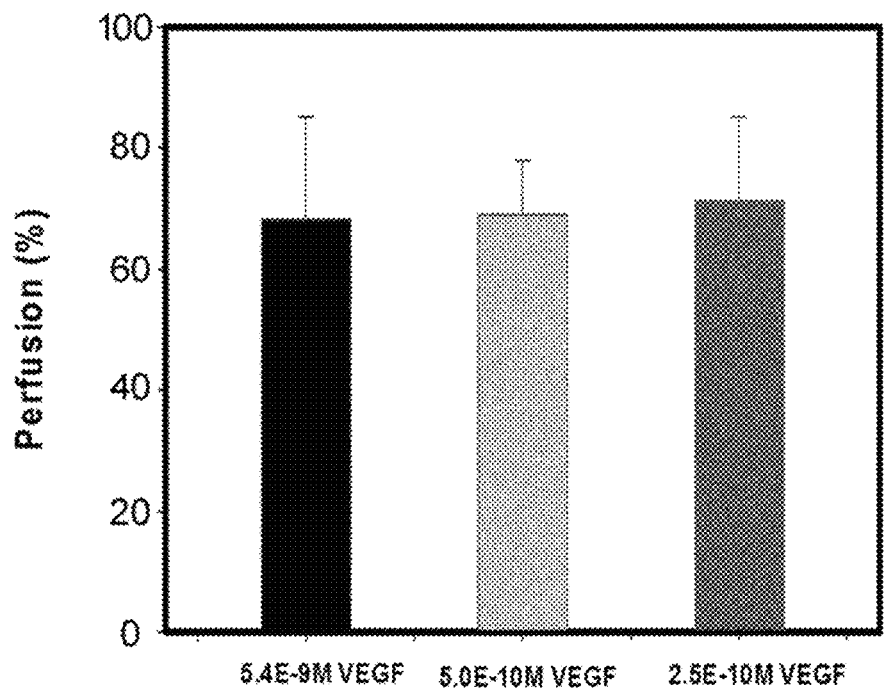
FIG. 7 shows data obtained by extracting heart tissues having ischemic lesions and measuring perfusion after one week has elapsed since the liposomes into which the VEGF-derived peptide is loaded at different concentrations {PEG-LP(VEGF)} are injected into rats having a myocardial infarction model.
Figure 8:
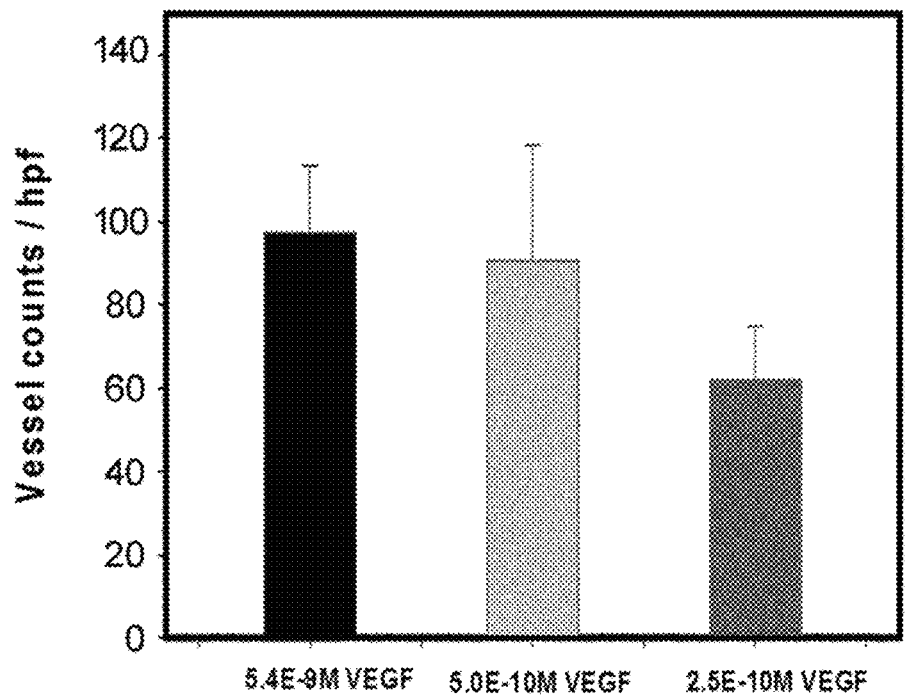
FIG. 8 shows data showing the total blood vessel counts obtained by extracting heart tissues having ischemic lesions and measuring the heart tissues through immunostaining after one week has elapsed since the liposomes into which the VEGF-derived peptide is loaded at different concentrations {PEG-LP(VEGF)} are injected into rats having a myocardial infarction model.
Figure 9:
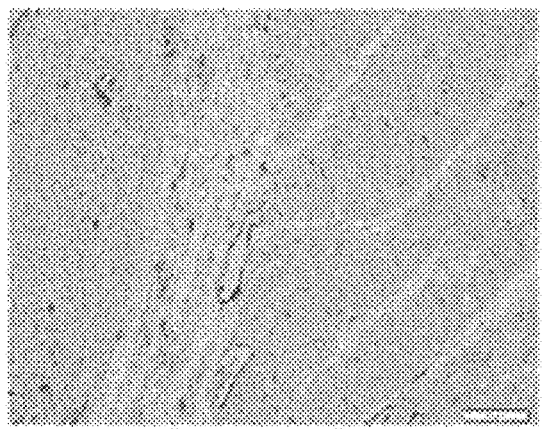
FIG. 9 is an image obtained by extracting heart tissues having ischemic lesions and observing the heart tissues through immunostaining after one week has elapsed since each of the control (PBS), a VEGF-derived peptide (VEGF) and the liposomes into which the VEGF-derived peptide is loaded at different concentrations {PEG-LP(VEGF)} is injected into rats having a myocardial infarction model.
Figure 9:
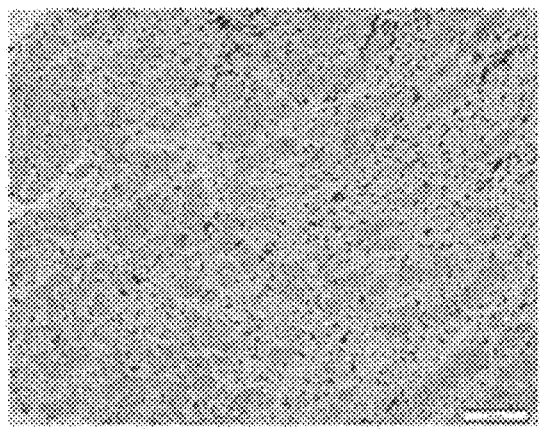
Figure 9:
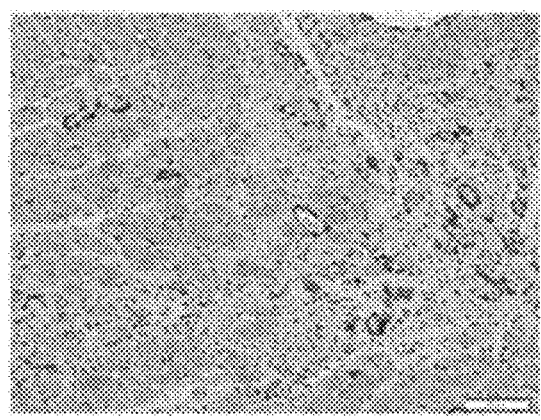
Figure 9:
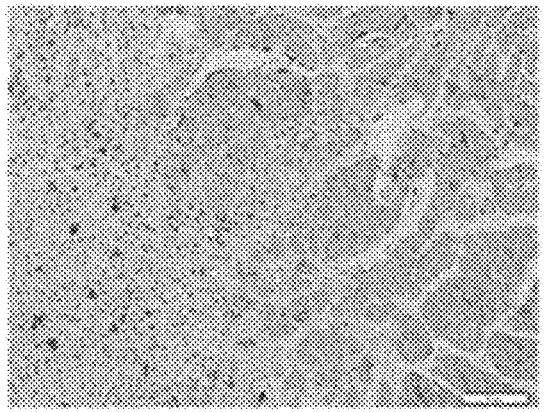
Figure 9:
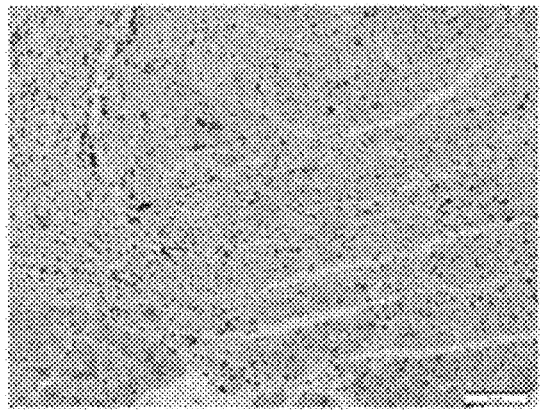

In the present invention, the VEGF-derived peptide may be included at a concentration of $2.5 \times 10^{-10}$ M or more. As shown in FIGS. 7 to 9, the release of VEGF is observed at different concentrations of the VEGF-derived peptide loaded into the liposomes. As a result, both of the perfusion-improving effect and the total vessel count-increasing effect are not observed to be significant due to a difference in concentration of the VEGF-derived peptide loaded into the liposomes.

That is, it is confirmed that the liposomes of the present invention, in which the VEGF-derived peptide is loaded at a concentration of $2.5 \times 10^{-10}$ M or more and which have a particle distribution of 50 to 200 nm and an average particle size of 90 to 110 nm and have a surface modified with polyethylene glycol, have an effective therapeutic effect on the ischemic lesions.

In the present invention, the term "ischemia" refers to a condition in which a blood flow is absolutely or relatively deficient as a source of oxygen with respect to the oxygen demand in tissues and organs. In this case, the ischemia in main organs due to atherosclerotic vascular occlusion causes severe diseases such as myocardial infarction, cerebral infarction, etc.

In the present invention, the "ischemic disease" may include all types of diseases caused by the ischemic condition, but the present invention is not limited thereto. Specifically, the ischemic disease may include one or more selected from the group consisting of myocardial infarction, middle cerebral artery occlusion, lower limb ischemia, and cerebral infarction, but the present invention is not limited thereto.

Figure 10:
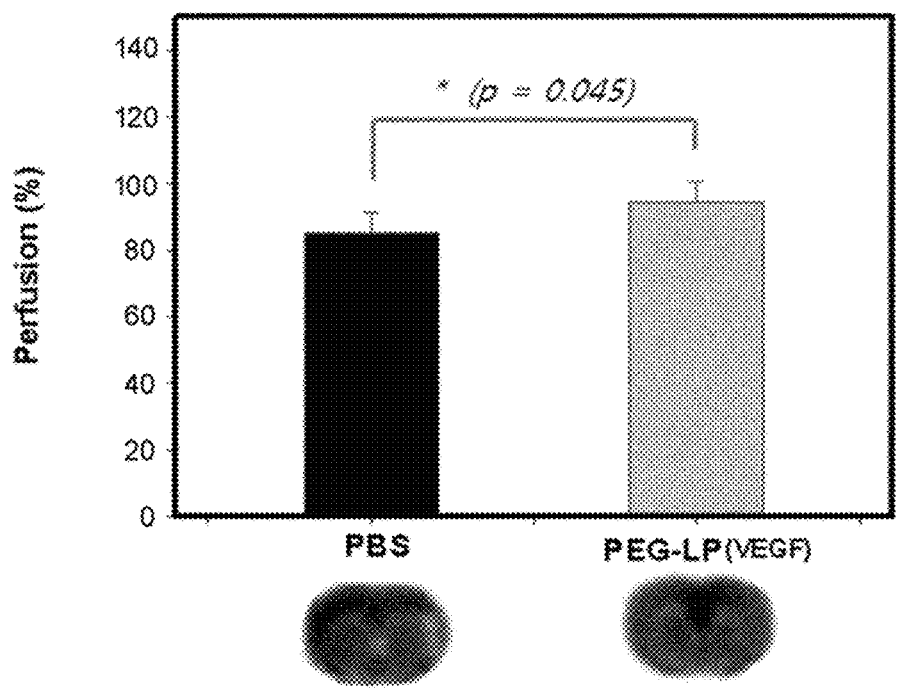
FIG. 10 shows data of measuring perfusion of brains having ischemic lesions after one week has elapsed since each of the control (PBS) and the liposomes of the present invention into which the VEGF-derived peptide is loaded {PEG-LP(VEGF)} is injected through common carotid arteries of rats having a middle cerebral artery occlusion model.
Figure 11:
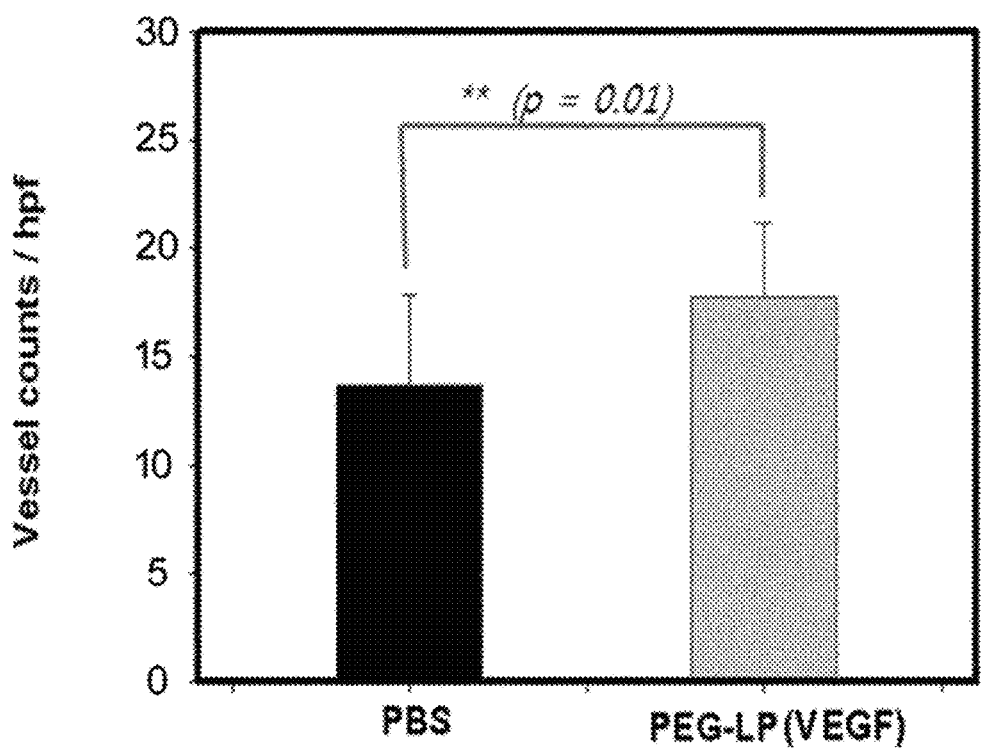
FIG. 11 shows data showing the total blood vessel counts obtained by extracting brain tissues having ischemic lesions and measuring the brain tissues through immunostaining after one week has elapsed since each of the control (PBS) and the liposomes of the present invention into which the VEGF-derived peptide is loaded {PEG-LP(VEGF)} is injected through common carotid arteries of rats having a middle cerebral artery occlusion model.
Figure 12:
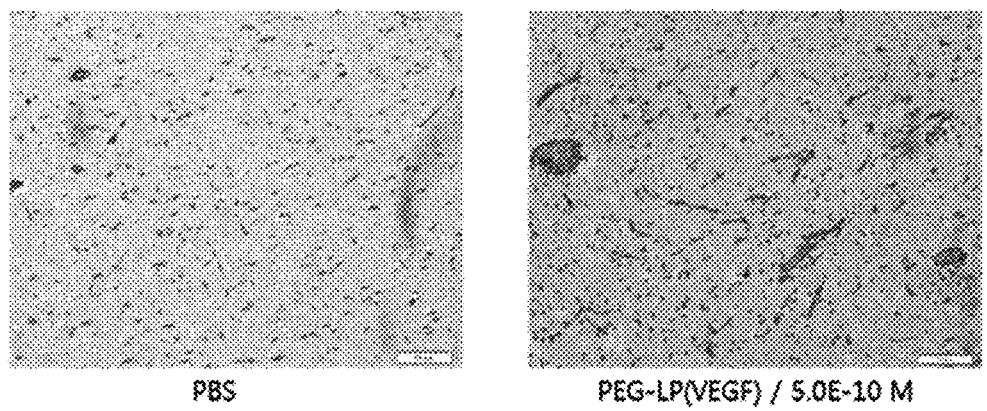
FIG. 12 is an image obtained by extracting brain tissues having ischemic lesions and observing the brain tissues through immunostaining after one week has elapsed since each of the control (PBS), a VEGF-derived peptide (VEGF) and the liposomes into which the VEGF-derived peptide is loaded at different concentrations {PEG-LP(VEGF)} is injected into rats having a middle cerebral artery occlusion model.

In the present invention, the results of FIGS. 1 to 9 show that the liposomes of the present invention into which the VEGF-derived peptide is loaded have a very effective therapeutic effect on myocardial infarction. Also, to check a therapeutic effect with respect to ischemic diseases other than myocardial infarction, a therapeutic effect with respect to transient middle cerebral artery occlusion (MCAO) is checked, as shown in FIGS. 10 to 12. As a result, it is confirmed that the perfusion is statistically significantly improved and the total vessel counts are increased in the group in which rats are treated with the liposomes into which the VEGF-derived peptide is loaded (LP-VEGF), compared to the control.

That is, the liposomes of the present invention into which the VEGF-derived peptide is loaded have a high therapeutic effect on the middle cerebral artery occlusion as well as the myocardial infarction, indicating that the liposomes into which the VEGF-derived peptide is loaded have a therapeutic effect on various ischemic lesion diseases.

A composition for preventing or treating an ischemic disease, which includes the liposomes of the present invention into which the VEGF-derived peptide is loaded may include one or more known active ingredients having a therapeutic effect on the ischemic diseases.

The pharmaceutical composition of the present invention may include a pharmaceutically acceptable carrier in addition to the active ingredients.

The carrier includes all types of standard pharmaceutical carriers used for known formulations such as a sterile solution, a tablet, a coated tablet, and a capsule, but the present invention is not limited thereto. Typically, such a carrier includes excipients such as lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, dextrin, milk, a certain type of clay, stearic acid, vegetable oil (e.g., edible oil, cottonseed oil, coconut oil, almond oil, peanut oil), a fatty ester such as a neutral fatty acid glyceride, mineral oil, Vaseline oil, animal fat and oil, cellulose derivatives (e.g., crystalline cellulose, hydroxypropyl cellulose, hydroxypropyl methylcellulose, methyl cellulose), and other known excipients. Such a carrier may also include an antioxidant, a humectant, a viscosity stabilizing agent, a flavoring agent, a color additive, and other components.

The composition of the present invention may be administered through any typical route of administration as long as the composition can reach a target tissue. The composition of the present invention may be administered through oral, intraperitoneal, intravenous, intramuscular, subcutaneous, intradermal, intranasal, intrapulmonary, rectal, intracavitary, and intradural administration, but the present invention is not limited thereto. The composition of the present invention may be administered daily or administered intermittently before the surgery, and may be administered in a single dose or 2 or 3 divided doses a day, but an administration mode and dosage of the composition may be properly chosen according to various methods typically known to those skilled in the related art in consideration of the type of disease, the dosage form, and the therapeutic effect, and the present invention is not limited thereto.

The liposomes of the present invention into which the VEGF-derived peptide is loaded may be administered in the form of an injectable formulation to treat ischemic diseases. Specifically, the liposomes of the present invention into which the VEGF-derived peptide is loaded may be directly injected into a lesion, or injected into an artery or vein so that the liposomes can be delivered to the lesion.

For parenteral administration, the composition of the present invention may include a sterile aqueous or non-aqueous solution, a dispersion, a suspension, or an emulsion, and also include a sterile powder re-prepared directly before use as the sterile solution or suspension. Examples of the proper sterile aqueous and non-aqueous carrier, the diluent, the solvent or the vehicle include water, physiological saline, ethanol, polyols (for example, glycerol, propylene glycol, polyethylene glycol, etc.) and a mixture thereof, vegetable oil (for example, olive oil), an injectable organic ester (for example, ethyl oleate), etc. For example, the certain sizes of the dispersion and suspension may be properly maintained using a coating material such as lecithin, and the fluidity of the dispersion and suspension may be properly maintained using a surfactant.

Also, the composition of the present invention may be used alone to treat the ischemic diseases, or may be used together with surgery, hormone therapy, drug treatment, and methods using a biological response modifier.

Also, the present invention provides a method for treating an ischemic disease, which includes administering the pharmaceutical composition to a subject suspected of having an ischemic disease.

In the present invention, the subject suspected of having an ischemic disease refers to a mammal including a rat, livestock, etc. as well as a human who has been diagnosed to have an ischemic disease or is at high risk of having the ischemic disease. However, subjects who may be cured by the pharmaceutical composition of the present invention are included without limitation. The pharmaceutical composition including the liposomes of the present invention into which the VEGF-derived peptide is loaded may be administered to a subject suspected of having an ischemic disease to effectively cure the subject. The ischemic disease is as described above.

In the present invention, the term "administration" means that the pharmaceutical composition of the present invention is introduced into a subject suspected of having an ischemic disease using any proper method. In this case, the pharmaceutical composition may be administered through various routes of oral or parenteral administration as long as the pharmaceutical composition can reach a target tissue.

For the objects of the present invention, the daily dose of the composition may be differently applied according to various factors including a specific therapeutically effective amount needed to achieve the type and level of a reaction for certain patients, a specific composition optionally used together with another preparation, the age, weight, general health conditions and sex of a patient, the diet, an administration time, a route of administration, a secretion rate of a composition, a treatment period, and a drug used together or simultaneously with the specific composition, and similar factors widely known in the field of medicine.

Also, the present invention provides a use of the liposomes into which the VEGF-derived peptide is loaded to prepare a drug for treating an ischemic disease, wherein the liposomes have a surface modified with polyethylene glycol, and have a particle distribution of 50 to 200 nm with an average particle size of 90 to 110 nm.

The configuration of the liposomes and the ischemic disease are as described above, and thus a description thereof is omitted to avoid excessive complexity in this specification.

Further, the present invention provides a kit for assessing a degree of delivery of the liposomes, into which the VEGF-derived peptide is loaded, to ischemic lesions and degrees of release and uptake of a loaded material, which includes (a) liposomes into which a VEGF-derived peptide is loaded; and (b) liposomes into which the VEGF-derived peptide is loaded and to which a chelate having a functional group capable of labeling PE of the liposomes with radioactive nuclides is bound. Here, the liposomes of (a) are labeled with a radioactive compound including radioactive nuclides, and the liposomes of (b) are labeled with the radioactive nuclides.

The chelate may include one or more selected from the group consisting of diethylenetriamine pentaacetic acid (DTPA), N-succinimidyl-3-[4-hydroxyphenyl]propionate (SHPP), histidine, tyrosine, and a protein including tyrosine, but the present invention is not limited thereto. For example, the chelate may vary depending on the radioactive nuclides.

The liposomes may be labeled with various radioactive nuclides or compounds including the radioactive nuclides, all of which are suitable for being detected by a nuclear imaging device.

The radioactive nuclides that may be used may, for example, include one or more selected from the group consisting of $^{99m}$Tc, $^{131}$I, $^{125}$I, $^{124}$I, $^{186}$Re, $^{188}$Re, $^{90}$Y, $^{166}$Ho, and $^{177}$Lu, but the present invention is not limited thereto. Among these, the $^{99m}$Tc ($^{99m}$technetium) is one of the radioactive isotopes used to label radioactive pharmaceuticals, has a relatively short half-life of 6 hours, and has low toxicity to human bodies since it releases gamma energy at 104 keV, the value of which is suitable for obtaining a gamma image. Also, the $^{99m}$Tc is very useful in obtaining an image due to high permeability when administered to the human body, may be used cheaply and conveniently because it can be produced in a generator, and thus has been applied to radioactive pharmaceuticals for diagnosis and treatment in the field of nuclear medicine.

The radioactive compound including the radioactive nuclides may, for example, include one or more selected from the group consisting of $^{99m}$Tc-hexamethyl propylene amine oxime ($^{99m}$Tc-HMPAO), a$^{99m}$Tc-ethyl cysteinate dimer ($^{99m}$Tc-ECD), $^{99m}$Tc-methylene diphosphonate ($^{99m}$Tc-MDP), $^{99m}$Tc-tetrofosmin, $^{99m}$Tc-2 methoxy-isobutyl-isonitrile ($^{99m}$Tc-MIBI), $^{99m}$TcO4$^-$, $^{99m}$Tc-macro-aggregated albumin ($^{99m}$Tc-MAA), $^{99m}$Tc-mercaptoacetyltriglycine ($^{99m}$Tc-MAG3), and $^{99m}$Tc-dimercaptosuccinic acid ($^{99m}$Tc-DMSA), but the present invention is not limited thereto.

According to one exemplary embodiment of the present invention, when the liposomes into which the VEGF is loaded are prepared, two types of the liposomes in which DTPA is bound and not bound to PE as a structural component of the liposomes may be prepared so that the liposomes to which DTPA is bound are labeled with $^{99m}$Tc-DTPA (diethylene tetramine penta-acetic acid) and the liposomes to which DTPA is not bound are labeled with $^{99m}$Tc-HMPAO (hexamethyl propylene amine oxime) to obtain a gamma image, thereby assessing a degree of delivery of the liposomes, into which the VEGF-derived peptide is loaded, to ischemic lesions and degrees of release and uptake of a loaded material.

When liposomes prepared in the present invention are treated with $^{99m}$Tc-HMPAO, the $^{99m}$Tc-HMPAO is loaded into the structure of the liposomes so that the liposomes are labeled with the $^{99m}$Tc-HMPAO like the VEGF-derived peptide. On the other hand, when the DTPA bound to the PE as the structural component of the liposomes is labeled with $^{99m}$Tc, the DTPA is labeled in the form of $^{99m}$Tc-DTPA bound to the structure of the liposomes.

FIG. 3 is a gamma image obtained 30 minutes after and 90 minutes after the liposomes labeled with the $^{99m}$Tc-HMPAO are injected into myocardial infarction model rats through an apical puncture. In this case, it is confirmed that the liposomes have a high uptake rate of 5.28% in the heart having ischemic lesions, as observed in the gamma image observed 30 minutes after injection of the liposomes. Because the heart tissues have a large amount of a blood pool, a gamma image is observed after a time sufficient for the disappearance of an effect of the $^{99m}$Tc-HMPAO or liposomes which are not absorbed into an ischemic lesion region, that is, 90 minutes after injection, in order to eliminate the effect. As a result, it is confirmed that the uptake rate into the heart having the ischemic lesions is 4.95%, the value of which is somewhat reduced, but still very high, compared to that 30 minutes after injection.

FIG. 6 shows data of comparing the uptake rates in the heart having ischemic lesions from a gamma image obtained after 90 minutes has elapsed since the liposomes of the present invention into which the VEGF-derived peptide is loaded {PEG-LP(VEGF)} are labeled with $^{99m}$Tc-HMPAO and $^{99m}$Tc-DTPA, respectively, and injected into rats having a myocardial infarction model. In this case, the uptake rate of the $^{99m}$Tc-HMPAO-labeled liposomes in the ischemic lesions represents the sum of a value of the $^{99m}$Tc-HMPAO loaded into the absorbed liposomes and a value of the $^{99m}$Tc-HMPAO released from the liposomes to be absorbed in the ischemic lesion, as observed in the gamma image.

On the other hand, it is confirmed that the uptake rate of the $^{99m}$Tc-labeled liposomes using DTPA represents a value of the liposomes absorbed in the ischemic lesion, which is lower than the value of the liposomes labeled with the $^{99m}$Tc-HMPAO. This indicates that the uptake of the liposomes occurs in the ischemic lesions. It is confirmed that a difference between a value of the liposomes labeled with $^{99m}$Tc-HMPAO and a value of the liposomes labeled with $^{99m}$Tc using DTPA is a value of $^{99m}$Tc-HMPAO released from the liposomes, and thus the release and uptake of the $^{99m}$Tc-HMPAO loaded into the liposomes occur at high levels.

Based on the aforementioned results, it is confirmed that the kit provided in the present invention is useful in assessing a degree of delivery of the liposomes, into which the VEGF-derived peptide is loaded, to ischemic lesions and degrees of release and uptake of a loaded material during a process of curing a patient suffering from ischemic diseases.

Hereinafter, the present invention will be described in detail with reference to preferred embodiments thereof so that any person having skill in the art to which the present invention belongs may easily put the present invention into practice. However, the present invention can be implemented in various different forms, and is not limited to the embodiments disclosed below.

EXAMPLES

Example 1

Preparation of Liposomes into which VEGF-derived Peptide is Loaded

In the present invention, liposomes (LP) into which a VEGF-derived peptide was loaded were prepared to increase a therapeutic effect of VEGF on ischemic diseases.

As the VEGF-derived peptide, a peptide consisting of an amino acid sequence of Ac-MRIKPHQGQHI-NH2 (SEQ ID NO: 1) was purchased from Peptron (Korea).

L-α-phosphatidylcholine (Egg-PC), cholesterol (CH) and L-glutathione were purchased from Sigma-Aldrich Chemical Co. (US) and used, {1,2-distearoyl-sn-glycero-3-phosphoethanolamine-N-[methoxy(polyethylene glycol)-2000]} (PEG2000-DSPE) and {1,2-distearoyl-sn-glycero-3-phosphoethanolamine-N-diethylenetriaminepentaacetic acid} (DTPA-DSPE) were purchased from Avanti Polar Lipids, Inc. (US) and used, and extra-pure chloroform and extra-pure methanol was purchased from Duck-San Pure Chemical Co., Ltd (Korea) and used.

Liposomes were prepared using a lipid thin-film hydration/extrusion method so that the Egg-PC, the cholesterol and the PEG2000-DSPE are present at a ratio of 50:40:10. The method was described in further detail, as follows. First, Egg-PC, cholesterol and PEG2000-DSPE were dissolved in a mixed solution of chloroform and methanol (7:3) to reach the aforementioned lipid ratio, and then evaporated at 51° C. for 4 hours to obtain a lipid thin film having a surface modified with polyethylene glycol. The obtained thin film was completely hydrated at 37° C. for an hour and a half in a PBS buffer solution (pH 7.4) to prepare liposomes (LP), and liposomes into which a VEGF-derived peptide was loaded {PEG-LP(VEGF)} were prepared using a PBS buffer solution including the VEGF-derived peptide.

Next, the prepared liposomes and the liposome into which the VEGF-derived peptide was loaded were extruded 20 times through polycarbonate membranes having pore sizes of 400 nm, 200 nm, 100 nm, and 50 nm using an Avanti mini extruder (Avanti Polar Lipids, Inc., US) in order to obtain small unilamellar vesicles.

The liposomes into which the VEGF-derived peptide was loaded thus prepared through the extrusion were subjected to size exclusion chromatography using a PD Midi-Trap G-25 column to remove free VEGF not loaded into the liposomes.

The loading efficiency of the VEGF-derived peptide in the liposomes into which the VEGF-derived peptide was loaded was measured using a difference in concentration of the VEGF-derived peptide solution before and after the hydration process, and an area of the VEGF-derived peptide was confirmed using high performance liquid chromatography (HPLC; Thermo Scientific, US) using a C18 silica gel column (5 μm, 10×250 mm; YMC, Japan).

Example 2

Evaluation of Therapeutic Efficacy of VEGF-derived Peptide and Liposomes into which VEGF-derived Peptide is Loaded with Respect to Myocardial Infarction In the present invention, an experiment on comparison with a group in which rats were treated with the VEGF-derived peptide alone was performed to check whether the liposomes into which the VEGF-derived peptide was loaded as prepared in Example 1 increased therapeutic efficacy with respect to ischemic diseases.

First, 8-week-old Sprague-Dawley rats were purchased from Orientbio Inc., and acclimated for 3 days under conditions such as a temperature of 22±3° C., a relative humidity of 60±20%, an air ventilation cycle of 10 to 20 times/hour, a 12-hour light/dark cycle (light on 08:00 A.M. and light off 08:00 P.M.), sterile feed, and water supplies. Thereafter, a myocardial infarction model was induced (Hwang H S et al., Radiology, 273(1):160, 2014), and 200 μL of each of the control (PBS), the VEGF-derived peptide (VEGF) and the liposomes of Example 1 into which the VEGF-derived peptide was loaded {PEG-LP(VEGF)} was injected into rats through an apical puncture, and the rats were bred for a week under the same breeding environment as in the pre-surgery environment. After a week, $^{99m}$technetium (Tc)-tetrofosmin was used as a myocardial perfusion imaging agent to obtain an autoradiographic images of rat hearts, and the relative perfusion was measured using a method represented by the following Equation 1 to evaluate an therapeutic effect of the VEGF-derived peptide.

Relative perfusion (%)={(Activity value of $^{99m}$Tc-tetrofosmin in cardiac ischemic area)/Activity value of $^{99m}$Tc-tetrofosmin in septum)}×100   [Equation 1]

Also, heart tissues having ischemic lesions were extracted, and the tissues obtained through a formalin-fixing process and a paraffin-embedding process were hydrated, and then subjected to von Willebrand factor immunohistochemical staining. Then, five images were randomly obtained using an optical microscope. The total vessel counts were measured from the obtained images to evaluate a therapeutic effect of the VEGF-derived peptide. The images were observed under a 200× high power field (HPF).

All the subsequent statistical analyses were performed using SAS ver. 9.2 (SAS Institute, Cary, US), the significance of difference was determined using a Duncan's multiple range test (MRT) and ANOVA, and a significant difference at $p<0.05$ was evaluated. All data was assumed to be significant within a range of 5%, and represented by an average±standard deviation (SD).

As a result, it was confirmed that the group in which the rats were treated with the VEGF-derived peptide alone had a perfusion-improving effect, compared to the control in which a PBS solution was injected into the rats, but significant results were not observed, as shown in FIG. 1. On the other hand, it was confirmed that the group in which the rats were treated with the liposomes into which the VEGF-derived peptide was loaded {PEG-LP(VEGF)} had a statistically significant (P=0.003) perfusion-improving effect, compared to the control.

Based on the comparison results of the total vessel counts, it was also confirmed that the total vessel counts were significantly increased in the group in which the rats were treated with the VEGF-derived peptide alone, compared to the control, as shown in FIG. 2. On the other hand, it was confirmed that the total vessel counts were statistically significantly increased in the group in which the rats were treated with the liposomes into which the VEGF-derived peptide was loaded {PEG-LP(VEGF)}, compared to the control.

This indicated that the liposomes as a drug delivery system were absorbed into ischemic lesion tissues so that an absorption of the VEGF-derived peptide into the ischemic lesion tissues is improved, compared to the group in which the rats were treated with the VEGF-derived peptide alone, thereby increasing the cardiac perfusion and the total vessel counts to enhance a therapeutic effect on the ischemic lesions. That is, it was confirmed that the liposomes of the present invention into which the VEGF-derived peptide was loaded improved a therapeutic effect on the ischemic diseases, compared to the group in which the rats were treated with the VEGF-derived peptide alone.

Example 3

Confirmation of Changes in Uptake Rate in Ischemic Lesions According to Time Elapsed after Injection of Liposomes into which VEGF-derived Peptide is Loaded In the present invention, the liposomes into which the VEGF-derived peptide was loaded were injected into rats having a myocardial infarction model, and a change in uptake rate in the ischemic lesions over time was then determined.

First, the liposomes prepared in Example 1 were labeled with $^{99m}$Tc-HMPAO (hexamethyl propylene amine oxime), and then injected into the myocardial infarction model rats induced in Example 2 through an apical puncture.

After 30 and 90 minutes had elapsed since injection, a gamma image was obtained using Symbia TruePoint SPECTCT gamma camera system (Siemens Healthcare, Erlangen, Germany), and the release and uptake rates of the VEGF-loaded liposomes and the loaded material in the ischemic lesions were compared.

As shown in FIG. 3, it was confirmed that a high uptake rate of 5.28% in the heart having ischemic lesions was observed in the gamma image obtained 30 minutes after injection of the liposomes. Because the heart tissues had a large amount of a blood pool, the gamma image was observed after a time sufficient for the disappearance of the effect of the $^{99m}$Tc-HMPAO or liposomes which were not absorbed into an ischemic lesion region, that is, 90 minutes after injection, in order to eliminate the effect. As a result, it was confirmed that the uptake rate into the heart having the ischemic lesions was 4.95%, the value of which was somewhat reduced but still very high, compared to that at 30 minutes after injection.

In the present invention, the values obtained 90 minutes after injection of the liposomes were compared to eliminate an effect of a blood pool of the heart in subsequent experiments and compare the results of the uptake in the ischemic lesions.

Example 4

Comparison of Uptake Rates in Ischemic Lesions According to Size of Liposomes into which VEGF-derived Peptide is Loaded In the present invention, an effect of the size of the liposomes into which the VEGF-derived peptide was loaded on the uptake in the ischemic lesion was checked.

First, liposomes into which the VEGF-derived peptide was loaded and which had a surface modified with PEG2000 were prepared in the same manner as in Example 1, except that the liposomes had average particle sizes of 100 nm, 300 nm and 600 nm. Thereafter, the liposomes were labeled with $^{99m}$Tc-HMPAO (hexamethyl propylene amine oxime) to measure an uptake rate.

FIG. 4 shows particle distributions of the liposomes into which the VEGF-derived peptide is loaded, the liposomes having average particle sizes of 100 nm, 300 nm and 600 nm, respectively. Here, it was confirmed that the liposomes had a particle distribution of 50 to 200 nm when the liposomes had an average particle size of 100 nm.

Next, 200 μL of each of the liposomes having different sizes as described above were injected into the myocardial infarction model rats induced in Example 2 through an apical puncture, and then the uptake rates were compared in the gamma image obtained after 90 minutes had elapsed.

As a result, as shown in FIG. 5, it was confirmed that the uptake rates in the ischemic lesions varied according to the particle size of the liposomes, and also confirmed that the liposome having an average particle size of 100 nm and a particle distribution of 50 to 200 nm had the highest uptake rate.

Example 5

Comparison of Uptake Rate of VEGF Released from Liposomes into which VEGF-derived Peptide is Loaded and Uptake Rate of Liposomes In the present invention, an uptake rate of VEGF released from the liposomes and an uptake rate of the liposomes into which the VEGF-derived peptide was loaded were compared using a modified radiolabeling method.

First, in a process of preparing the liposome, which had an average particle size of 100 nm and a particle distribution of 50 to 200 nm and had a surface modified with PEG2000, using the method of Example 1, a lipid thin film was hydrated in a solution in which L-glutathione was dissolved to prepare the liposomes. Thereafter, the liposomes were mixed with $^{99m}$Tc-HMPAO (hexamethyl propylene amine oxime), and the resulting mixture was sufficiently stirred for 30 minutes to obtain the liposomes labeled with $^{99m}$Tc-HMPAO. The liposomes were washed with PBS using a centrifuge, and $^{99m}$Tc-HMPAO which was not loaded into the liposomes was removed through size exclusion chromatography using a PD Midi-Trap G-25 column. As another method, 1,2-distearoyl-sn-glycero-3-phosphoethanolamine-N-diethylenetriaminepentaacetic acid (DTPA-PE) in which diethylene tetramine penta-acetic acid (DTPA) was bound to PE as a component of a liposome lipid layer was purchased from Avanti Polar Lipids, Inc. (US) and used to prepare liposomes. Then, the liposomes were labeled with $^{99m}$Tc using a small amount of $SnCl_2$ (Sigma Aldrich) dissolved in a 0.1 N HCl solution.

200 μL of each of the liposomes labeled through the two methods was injected into the myocardial infarction model rats induced in Example 2 through an apical puncture, and then the uptake rates were compared from the gamma image obtained after 90 minutes had elapsed.

When the liposomes were treated with $^{99m}$Tc-HMPAO, the $^{99m}$Tc-HMPAO was loaded into the structure of the liposomes so that the liposomes were labeled with the $^{99m}$Tc-HMPAO like the VEGF-derived peptide. On the other hand, when DTPA bound to the structural component (PE) of the liposomes was labeled with $^{99m}$Tc, the DTPA was labeled in the form of $^{99m}$Tc-DTPA bound to the structure of the liposomes.

As shown in FIG. 6, the uptake rate of the liposomes labeled with $^{99m}$Tc-HMPAO in the ischemic lesions was the sum of a value of $^{99m}$Tc-HMPAO loaded into the absorbed liposomes and a value of $^{99m}$Tc-HMPAO released from the liposomes and absorbed in the ischemic lesions, as observed in the gamma image.

On the other hand, it was confirmed that the uptake rate of the $^{99m}$Tc-labeled liposomes using DTPA was a value of the liposomes absorbed in the ischemic lesions, which was lower than the value of the liposomes labeled with the $^{99m}$Tc-HMPAO. This indicated that the uptake of the liposomes occurred in the ischemic lesions. Thus, it was confirmed that a difference between a value of the liposomes labeled with $^{99m}$Tc-HMPAO and a value of the liposomes labeled with $^{99m}$Tc using DTPA was a value of $^{99m}$Tc-HMPAO released from the liposomes, and thus the release and uptake of the $^{99m}$Tc-HMPAO loaded into the liposomes occurred at high levels.

Example 6

Evaluation of Therapeutic Efficacy on Ischemic Diseases According to Concentration of VEGF-derived Peptide Loaded into Liposomes In the present invention, a therapeutic effect of the liposomes on ischemic diseases according to the concentration of the VEGF-derived peptide loaded into the liposomes was checked.

First, liposomes having an average particle size of 100 nm and a particle distribution of 50 to 200 nm and having a surface modified with PEG2000 were prepared in the same manner as in Example 1 so that the concentration of the VEGF-derived peptide reached $2.5 \times 10^{-10}$ M, $5.0 \times 10^{-10}$ M, and $5.4 \times 10^{-9}$ M.

200 μL of each of the aforementioned liposomes was injected into the myocardial infarction model rats induced in Example 2 through an apical puncture, a cardiac perfusion image was observed in the same manner as in Example 2, and the relative perfusion was measured to evaluate a therapeutic effect of the VEGF-derived peptide.

Also, the total vessel counts were measured in the same manner as in Example 2 to evaluate a therapeutic effect of the VEGF-derived peptide.

As a result, as shown in FIG. 7, it was confirmed that, because there was no statistically significant difference in the cardiac perfusion results even when the concentration of the VEGF-derived peptide loaded into the liposomes was reduced, the liposomes of the present invention into which the VEGF-derived peptide was loaded had a therapeutic effect on the ischemic lesions even when the VEGF-derived peptide was present at a low concentration.

Also, as shown in FIG. 8, no significant difference in the total vessel counts due to the difference in concentration of the VEGF-derived peptide loaded into the liposomes was observed when the total vessel counts were compared.

FIG. 9 is an image obtained by observing the tissues through immunostaining. Here, it was confirmed that the total vessel counts increased due to the neovascularization when the tissues were treated with the liposomes into which the VEGF-derived peptide was loaded, regardless of the concentration of the VEGF-derived peptide.

That is, based on the results, it was confirmed that the liposomes, into which the VEGF-derived peptide was loaded at a concentration of $2.5 \times 10^{-10}$ M or more and which had an average particle size of 100 nm and a particle distribution of 50 to 200 nm particle distribution and had a surface modified with PEG2000, had an effective therapeutic effect on the ischemic lesions.

Example 7

Evaluation of Therapeutic Efficacy of Liposome into which VEGF-derived Peptide is Loaded with Respect to Middle Cerebral Artery Occlusion In the present invention, it was determined whether the liposomes into which the VEGF-derived peptide was loaded had a therapeutic effect on ischemic diseases other than myocardial infarction.

First, the VEGF-derived peptide was loaded into the liposomes at a concentration of $5.0 \times 10^{-10}$ M in the same manner as in Example 1, and liposomes having an average particle size of 100 nm and a particle distribution of 50 to 200 nm and having a surface modified with PEG2000 were finally prepared.

Next, 8-week-old Sprague-Dawley rats were purchased from Orientbio Inc. to induce a transient middle cerebral artery occlusion (MCAO) model (Nagasawa H et al., Stroke; a journal of cerebral circulation, 20:1037. 1989; Bunevicius A et al., BioMed Research International, 2013:634598, 2013), and 200 μL of each of the control (PBS) and the liposomes into which the VEGF-derived peptide was loaded was injected through common carotid arteries. Thereafter, perfusion images of the brains having ischemic lesions were observed in the same manner as in Example 2, and the relative perfusions were then measured to evaluate a therapeutic effect of the VEGF-derived peptide.

Also, the total vessel counts were measured in the same manner as in Example 2 to evaluate a therapeutic effect of the VEGF-derived peptide.

As shown in FIG. 10, it was confirmed that the group in which the rats were treated with the liposomes into which the VEGF-derived peptide was loaded {PEG-LP(VEGF)} had a statistically significant (P=0.003) perfusion-improving effect, compared to the control in which a PBS solution was injected into the rats.

Also, as shown in FIG. 11, it was confirmed that the group in which the total vessel counts were statistically significantly increased (P=0.01) in the rats were treated with the liposomes into which the VEGF-derived peptide was loaded {PEG-LP(VEGF)}, compared to the control. FIG. 12 is an image obtained by observing the tissues through immunostaining. Here, it was confirmed that new blood vessels were generated in the middle cerebral artery occlusion when the tissues were treated with the liposomes into which the VEGF-derived peptide was loaded, resulting in increased total vessel counts.

That is, it was confirmed that the liposomes of the present invention, into which the VEGF-derived peptide was loaded and which had an average particle size of 100 nm and a particle distribution of 50 to 200 nm and had a surface modified with PEG2000, had a high therapeutic effect on the middle cerebral artery occlusion as well as the myocardial infarction, indicating that the liposomes into which the VEGF-derived peptide was loaded had a therapeutic effect on various ischemic lesion diseases.

Although the preferred embodiments of the present invention have been shown and described in detail, it will be appreciated by those skilled in the art that the detailed description and specific examples are given by way of illustration only without departing from the principles and spirit of the disclosure, the scope of which is defined in the claims and their equivalents.

According to the present invention, the composition for preventing or treating an ischemic disease, which includes the liposomes into which the VEGF-derived peptide is loaded and which have a particle distribution of 50 to 200 nm with an average particle size of 90 to 110 nm and have a surface modified with polyethylene glycol, can remarkably increase the uptake of VEGF, compared to when treated with VEGF alone, and thus can be used to effectively treat ischemic diseases such as myocardial infarction, middle cerebral artery occlusion, lower limb ischemia, and cerebral infarction. Also, the liposome kit including DTPA-PE provided in the present invention can be useful in assessing a degree of delivery of the liposomes, in which the VEGF-derived peptide is loaded, to ischemic lesions and degrees of release and uptake of a loaded material during a process of curing a patient suffering from ischemic diseases.

The invention claimed is:

1. A pharmaceutical composition for preventing or treating an ischemic disease, comprising;

(a) liposomes loaded with a vascular endothelial growth factor (VEGF)-derived peptide consisting of the amino acid sequence of SEQ ID NO:1; or
(b) liposomes loaded with a vascular endothelial growth factor (VEGF)-derived peptide consisting of the amino acid sequence of SEQ ID NO:1, the liposome having a chelate bound to phosphatidylethanolamine (PE) of the liposome, the chelate having a functional group capable of being labeled with radioactive nuclides,
wherein the liposomes (a) and (b) have a surface modified with polyethylene glycol, and have a particle distribution of 50 to 200 nm with an average particle size of 90 to 110 nm, and
wherein the liposomes of (a) are labeled with a radioactive compound comprising radioactive nuclides, and the chelate bound to phosphatidylethanolamine (PE) of the liposomes of (b) is labeled with radioactive nuclides.

2. The pharmaceutical composition of claim 1, wherein the VEGF-derived peptide is included at a concentration of $2.5 \times 10^{-10}$ M or more.

3. The pharmaceutical composition of claim 1, wherein the polyethylene glycol has a molecular weight of 1,800 g/mol to 2,200 g/mol.

4. The pharmaceutical composition of claim 1, wherein the ischemic disease comprises one or more selected from the group consisting of myocardial infarction, middle cerebral artery occlusion, lower limb ischemia, and cerebral infarction.

5. The pharmaceutical composition of claim 1, wherein the composition is an injectable formulation.

6. A kit for assessing a degree of delivery of liposomes, into which a VEGF-derived peptide is loaded, to ischemic lesions and degrees of release and uptake of a loaded material, comprising:

(a) liposomes loaded with a VEGF-derived peptide; and
(b) liposomes loaded with the VEGF-derived peptide is loaded, wherein a chelate having a functional group capable of being labeled with radioactive nuclides is bound to phosphatidylethanolamine (PE) of the liposome,
wherein the VEGF-derived peptide consists of the amino acid sequence of SEQ ID NO: 1 and the liposomes of (a) are labeled with a radioactive compound comprising radioactive nuclides, and the chelate bound to the PE of the liposomes of (b) is labeled with the radioactive nuclides.

* * * * *